(12) United States Patent
Ohkouchi (10) Patent No.: US 9,060,988 B2
(45) Date of Patent: Jun. 23, 2015

(54) METHOD FOR TREATING PULMONARY FIBROSIS USING A PHARMACEUTICAL COMPOSITION CONTAINING STANNIOCALCIN 1 (STC1)

(75) Inventor: Shinya Ohkouchi, Miyagi (JP)

(73) Assignee: Tohoku University, Miyagi (JP)

( * ) Notice: Subject to any disclaimer, the term of this patent is extended or adjusted under 35 U.S.C. 154(b) by 0 days.

(21) Appl. No.: 14/130,387

(22) PCT Filed: Jul. 3, 2012

(86) PCT No.: PCT/JP2012/066971
§ 371 (c)(1),
(2), (4) Date: Dec. 31, 2013

(87) PCT Pub. No.: WO2013/008681
PCT Pub. Date: Jan. 17, 2013

(65) Prior Publication Data
US 2014/0135266 A1    May 15, 2014

(30) Foreign Application Priority Data
Jul. 9, 2011    (JP) .................................. 2011-152392

(51) Int. Cl.
*A61K 38/16*    (2006.01)
*A61K 38/22*    (2006.01)

(52) U.S. Cl.
CPC ...................................... *A61K 38/22* (2013.01)

(58) Field of Classification Search
None
See application file for complete search history.

(56) References Cited

U.S. PATENT DOCUMENTS

2004/0254102 A1    12/2004    Yoshiko et al.
2010/0221746 A1    9/2010    Phillips et al.

FOREIGN PATENT DOCUMENTS

| EP | 1 121 936 A1 | 8/2001 |
|---|---|---|
| EP | 1 304 117 A1 | 4/2003 |
| JP | 7-188051 A | 7/1995 |
| JP | 2000-229880 A | 8/2000 |
| WO | 00/16795 A1 | 3/2000 |
| WO | 02/04013 A1 | 1/2002 |
| WO | 2010/051347 A1 | 5/2010 |

OTHER PUBLICATIONS

International Search Report for corresponding International Application No. PCT/JP2012/066971, mailed Aug. 21, 2012 (3 pages).
I Samudio et al.; "The Warburg Effect in Leukemia-Stroma Cocultures Is Mediated by Mitochondrial Uncoupling Associated with Uncoupling Protein 2 Activation;" American Association for Cancer Research; Jul. 1, 2008; pp. 5198-5205 (9 pages).
I Samudio et al.; "Mitochondrial Uncoupling and the Warburg Effect: Molecular Basis for the Reprogramming of Cancer Cell Metabolism;" American Association for Cancer Research; Mar. 3, 2009; pp. 2163-2166 (5 pages).
Respiratory Medicine et al.; "Novel funtions of stanniocalcin-1 (STC1) through Uncoupling Protein 2 (UCP2) up-regulation; Promoting Survival of Cancer Cells under Oxidative Stress and Inducing the Uncoupling Respiration (Warburg Effect).;" Tohoku University Global COE; Sendai, Japan; Feb. 5, 2011 (15 pages).
Y. Wang et al.; "Stanniocalcin-1 suppresses superoxide generation in Macrophages through induction of mitochondrial UCP2;" JLB; vol. 86; Oct. 2009; pp. 981-988 (8 pages).
L. Huang et al.; "Anti-Inflammatory and Renal Protective Actions of Stanniocalcin-1 in a Model of Anti-Glomerular Basement Membrane Glomerulonephritis;" The American Journal of Pathology, vol. 174, No. 4; Apr. 2009; (11 pages).
L. Ortiz et al.; "Mesenchymal stem cell engraftment in lung is enhanced in response to bleomycin exposure and ameliorates its fibrotic effects;" PNAS;, vol. 100, No. 14; Jul. 8, 2003; pp. 8407-8411 (5 pages).
S Hagiwara et al.; "Aerosolized Administration of N-Acetylcysteine Attenuates Lung Fibrosis Induced by Bleomycin in Mice;" Am J Respir Crit Care Med; vol. 162; 2000; pp. 225-231 (7 pages).
M. Ebina; "Animal experimental model of pulmonary fibrosis;" Respiration and Circulation, vol. 56, No. 9, Sep. 2008; pp. 893-899 (16 pages).
A. Matsumoto; "Idiopathic pulmonary fibrosis;" Nippon Rinsho; vol. 64, No. 7; 2006; pp. 1354-1360 (17 pages).
EPO Communication (Office Action) issued Feb. 25, 2015, by the European Patent Office in corresponding European Patent Application No. EP-12812138.1 (1 page), with the Extended European Search Report dated Feb. 17, 2015 (6 pages).

*Primary Examiner* — Christine J Saoud
(74) *Attorney, Agent, or Firm* — Osha Liang LLP (57) ABSTRACT

A pharmaceutical composition for treating fibrosis and/or the progression of fibrosis contains stanniocalcin 1 (STC1) as an active ingredient; or a pharmaceutical composition for treating pulmonary fibrosis and/or suppressing the progression of pulmonary fibrosis contains STC1 as an active ingredient. A method for treating or suppressing progression of fibrosis using the above pharmaceutical composition. The fibrosis may be pulmonary fibrosis.

1 Claim, 7 Drawing Sheets

Fig 3 Bleo

Fig 4

Fig5 NAC

Fig6

METHOD FOR TREATING PULMONARY FIBROSIS USING A PHARMACEUTICAL COMPOSITION CONTAINING STANNIOCALCIN 1 (STC1)

CROSS REFERENCES TO RELATED APPLICATIONS

This is a national stage application of PCT/JP2012/066971, filed on Jul. 3, 2012, which claims the priority of Japanese application No. 2011-152392, filed on Jul. 9, 2011. This application claims the benefit and priority of these prior applications and incorporates these prior applications by reference in their entireties.

TECHNICAL FIELD

The present invention relates to a pharmaceutical composition for preventing, suppressing the progression of, and/or treating fibrosis, particularly pulmonary fibrosis.

BACKGROUND ART

Interstitial pneumonia is a refractory disease characterized by inflammation in the interstitial tissue of the lung (parts other than the pulmonary alveoli). It is known that in 50% of the patients with interstitial pneumonia, the disease' switches over to idiopathic pulmonary fibrosis and progresses in severity. Pulmonary fibrosis is a disease in which the lung becomes stiff and then shrinks, thereby the gas exchange becomes insufficient. When these symptoms progress, the patient finally suffers from respiratory distress, which leads to death. It is reported that there are 15,000 idiopathic pulmonary fibrosis patients in Japan, while there are 50,000 patients in the United States.

Currently, in regard to this disease, there has been a strong demand from patients and physicians for an effective drug or therapy, and pharmaceutical companies have paid attention thereto and put efforts into research and development. Nevertheless, there has been no effective medicament or therapeutic method established heretofore, and the survival time lasts 2 to 3 years.

Stanniocalcin 1 (STC1) is a dimeric glycoprotein hormone which was discovered in the gills of fishes and is also found in mammals. In addition to its role in the metabolism of phosphorus and calcium, STC1 is known to have various physiological activities, such as promotion of oxidative phosphorylation in mitochondria, a neuron and cardiac muscle protecting action, and a bone metabolism promoting action.

Specifically, the following findings have been reported. STC1 decreases the membrane potential of mitochondria in the cells through induction of uncoupling protein 2 (UCP2) (Non-Patent Documents 1 to 3). This decrease in the mitochondrial membrane potential via UCP2 leads to a decrease in intracellular peroxides (ROS), and brings about a decrease in the glucose dependency of mitochondria and an increase in lipid metabolism by mitochondria (Non-Patent Documents 1 to 3). Furthermore, STC1 induces uncoupling metabolism (resulting in an increase in the amount of lactic acid, an increase in the amount of oxygen consumption, and an increase in the amount of lipid metabolism), which is neither anaerobic metabolism nor aerobic metabolism. Uncoupling metabolism enables consumption of more energy and reduces peroxidation stress under the condition of starvation (or a disturbed environment), and therefore, it is believed that uncoupling metabolism is advantageous in the survival in a disturbed environment (Non-Patent Documents 3 and 4).

Non-Patent Document 5 and Patent Document 1 disclose that in a nephritis model mouse produced by administering a substance inducing nephritis (Anti-GBM Ab), fibrosis occurs in the kidney tissue of the mouse. It is also described that when a nephritis-inducing substance was administered respectively to a wild type (WT) mouse and a STC1-overexpressing mouse, it was demonstrated that the extent of fibrillization of the kidney tissue had been reduced in the kidney of the STC1-overexpressing mouse than in that of the WT mouse.

However, in this experiment using a model mouse, fibrillization occurred as a result of the inflammation of nephritis, and the inflamed tissue of the kidney was fibrillized. In these documents, there is no description indicating that STC1 has an anti-fibrotic action (fibroblast proliferation inhibiting action or the like). Furthermore, there is no description on pulmonary fibrosis.

In regard to STC1, utilization thereof has been proposed as pharmaceutical compositions based on the various physiological activities such as the adipocyte differentiation or maturation inhibitory activity, the promoting action of bone formation and the neuron protective action (Patent Documents 2 to 5). However, no relevant prior art that suggests the potential as a medicine for pulmonary fibrosis has been found.

CITATION LIST

Patent Documents

Patent Document 1: WO 2010/051347
Patent Document 2: Japanese Patent Application Laid-Open (JP-A) No. 2000-229880
Patent Document 3: JP-A No. H07-188051
Patent Document 4: Japanese republication of PCT International Publication No. 02/004013 (WO02/004013)
Patent Document 5: Japanese republication of PCT International Publication No. 00/016795 (WO00/016795)

Non-Patent Documents

Non-Patent Document 1: Cancer Res., 2008, 68:(13) 5198-5205
Non-Patent Document 2: Cancer Res., 2009, 69:(6) 2163-2166
Non-Patent Document 3: Tohoku University Global COE Network Medicine Winter Camp of GCOE 2010, Feb. 5$^{th}$ 2011, Akiu, Sendai, Japan
Non-Patent Document 4: Journal of Leukocyte Biology, 2009, 86:981-988
Non-Patent Document 5: The American Journal of Pathology, 2009, 174:(4) 1368-1378
Non-Patent Document 6: Kokyu to Junkan (Respiration and Circulation) (Igaku Shoin, Ltd.), September Issue, 2008, Hai Senisho no Dobutsu Jikken Moderu (Animal experimental model for pulmonary fibrosis (Masahito EBINA))
Non-Patent Document 7: PNAS, 2003:(14) 8407-8411
Non-Patent Document 8: AJRCCM, 2000:(162) 225-231

SUMMARY OF INVENTION

Problem to be Solved by the Invention

It is an object of the present invention to provide a pharmaceutical composition which is useful as a prophylactic and therapeutic agent for fibrosis, particularly pulmonary fibrosis.

Means for Solving Problem

Since STC1 reduces the ROS stress, the present inventors conducted research in expectation of a possibility that STC1 may prolong the survival of lung cells or activate the function of lung cells under a low-oxygen condition. As a result, the inventors found that fibrillization of the lung is markedly suppressed in an experimental pulmonary fibrosis model mouse to which STC1 has been intratracheally administered, thus completing the present invention.

Therefore, according to the present invention, provided are:

[1] a pharmaceutical composition for preventing, treating and/or suppressing the progression of fibrosis, which contains STC1 as an active ingredient; and

[2] the pharmaceutical composition according to the above item [1], wherein the fibrosis is pulmonary fibrosis.

Effect of the Invention

According to the pharmaceutical composition of the present invention, fibrillization of the lung is markedly suppressed, and along with this, peroxidation stress is markedly suppressed. Therefore, the pharmaceutical composition of the present invention enables prevention, suppression of progression, and/or treatment of fibrosis, particularly pulmonary fibrosis.

STC1 is advantageous as compared with conventional drugs that may also be utilized in the amelioration of fibrosis. Since predonine, cyclosporin A, FK506 and the like strongly suppress immunity, these drugs are causative of susceptibility to infection. In contrast to this, it has been reported that STC1 does not cause suppression of the immune system (Transgenic Res. (2010) 19:1017-1039), and therefore, it is expected that STC1 would not result in the susceptibility to infection. Furthermore, STC1 is believed to be advantageous when compared to N-acetylcysteine (NAC) in that NAC has a defect that it cannot be intravenously administered.

BEST MODE(S) FOR CARRYING OUT THE INVENTION

The pharmaceutical composition for the prevention or treatment of fibrosis of the present invention is characterized by containing STC1 as an active ingredient. The STC1 used in the present invention may be any of natural STC1 molecule obtainable from animal cells, tissues and the like; a recombinant type STC1 having the same amino acid sequence as that of natural STC1; a recombinant type STC1 produced based on a genetically engineered STC1 gene; synthesized STC1; and a functional equivalent such as an active fragment of STC1. Therefore, the term "stanniocalcin 1" (STC1) according to the present invention is used to mean to include these various types of STC1 as well, unless particularly stated otherwise.

The STC1 used in the present invention is preferably an STC1 having the amino acid sequence of human origin, or an STC1 which is modified without impairing the function based on the human-derived amino acid sequence. The amino acid sequence and base sequence of human STC1 are known and are registered with the Bank under the Accession numbers of NP#003146.1 and NM#003155.2. Also for STC1s of animals other than *Homo sapiens*, the amino acid sequences and base sequences of many animal-derived STC1s are known, and these are known to exhibit high homology with human STC1 such as, for example, 94% of fish (*Oncorhynchus kisutch*), 95% of birds (*Gallus Gallus*), and 100% of various mammals (Table 1).

TABLE 1

| Gene No. | Animal Species | Homology |
| --- | --- | --- |
| NP 003146.1 | stanniocalcin-1 [*Homo sapiens*; human] | 100% |
|  | stanniocalcin 1 [*Pan troglodytes*; ape] |  |
| XP 001106526.1 | PREDICTED: stanniocalcin-1 isoform 2 [*Macaca mulatta*; Cercopithecus] | 100% |
| XP 543238.2 | PREDICTED: similar to Stanniocalcin-1 precursor (STC-1) [*Canis familiaris*; dog] | 100% |
| XP 002914812.1 | PREDICTED: stanniocalcin-1-like [*Ailuropoda melanoleuca*; panda] | 100% |
| NP 033311.3 | stanniocalcin 1 [*Mus musculus*; mouse] | 100% |
| NP 112385.1 | stanniocalcin 1 [*Rattus norvegicus*; rat] | 100% |
| XP 001493245.1 | PREDICTED: similar to Stanniocalcin-1 precursor (STC-1) [*Equus caballus*; horse] | 100% |
| NP 001096682.1 | stanniocalcin-1 [*Sus scrofa*; pig] | 100% |
| XP 002756880.1 | PREDICTED: stanniocalcin-1-like [*Callithrix jacchus*; marmoset] | 100% |
| NP 788842.2 | stanniocalcin-1 precursor [*Bos taurus*; cattle] | 100% |
| XP 001506746.1 | PREDICTED: similar to stanniocalcin [*Ornithorhynchus anatinus*; platypus] | 100% |
| XP 425760.2 | PREDICTED: similar to stanniocalcin [*Gallus gallus*; chicken] | 95% |
| XP 001373050.1 | PREDICTED: similar to stanniocalcin [*Monodelphis domestica*] | 99% |
| XP 002709510.1 | PREDICTED: stanniocalcin 1 [*Oryctolagus cuniculus*] | 100% |
| NP 001088352.1 | stanniocalcin 1 [*Xenopus laevis*] | 89% |
| BAC66163.1 | stanniocalcin [*Amia calva* (fish)] | 81% |
| BAC66164.1 | stanniocalcin [*Lepisosteus osseus* (fish)] | 80% |
| NP 001038922.1 | stanniocalcin 1 [*Danio rerio*; zebrafish] | 81% |

TABLE 1-continued

| Gene No. | Animal Species | Homology |
|---|---|---|
| ACA35030.1 | stanniocalcin 1-B [*Tetraodon nigroviridis*] | 91% |
| P18301.2 | Stannius protein [*Anguilla australis*; eel] | 81% |
| Q08264.1 | stanniocalcin [*Oncorhynchus kisutch*; coho salmon] | 94% |
| NP 001117762.1 | stanniocalcin [*Oncorhynchus mykiss*; rainbow trout] | 94% |
| ABI64157.1 | stanniocalcin-1 [*Paralichthys olivaceus*; flounder] | 96% |
| AAV58802.1 | stanniocalcin [*Platichthys flesus*] >gb|AAV58803.1| stanniocalcin [*Platichthys flesus*; plaice] | 96% |

Therefore, the STC1 that can be used in the present invention is an STC1 having at least 80% homology, preferably at least 90% homology, and most preferably at least 94% homology, with the amino acid sequence of human STC1. Particularly, it is preferable to use a natural or recombinant STC1 (rSTC1) having an amino acid sequence that is 100% coincident with the human STC1 sequence (for example, 293 cell-derived human STC1 sequence). In the present invention, one or more kinds of these STC1s can be appropriately selected and used.

The pharmaceutical composition of the present invention contains STC1 as the only essential ingredient, but if desired, it may contain a component that is considered to have an effective action for amelioration of fibrosis. Examples include a steroid preparation such as predonine; a reducing agent such as N-acetylcysteine; an antifibrotic drug such as pirfenidone; an immunosuppressive drug such as cyclosporine A or FK506; and components for glucose infusion solution and Ringer's infusion solution. When these other effective ingredients are further incorporated, a superior fibrosis-ameliorating action can be expected. Also, the pharmaceutical composition of the present invention can be used in combination with these drugs.

Meanwhile, the term "amelioration" of fibrosis in terms of the present invention is used to mean to include prevention and treatment (including remission and cure).

The pharmaceutical composition of the present invention can be administered by formulating the composition using various components that are known in the pharmaceutical industry or food industry. The route of administration may be any known oral or parenteral route, and for example, any route such as oral, percutaneous, injection, enteric or intrarectal route can be selected. Preferred examples of the route of administration include tracheal administration, and oral administration or injection or infusion, as in the case of hormone preparations.

Therefore, examples of the dosage form of the pharmaceutical composition include compositions for injection, compositions for infusion, suppositories, transnasal preparations, sublingual preparations, and percutaneous absorption preparations. In the pharmaceutical composition of the present invention, an excipient, a disintegrant, a lubricating agent, a binding agent, a surfactant, a fluidity promoting agent, a colorant, a stabilizer, a flavor and the like that are known in the pharmaceutical industry may be appropriately added as additives, and thereby a pharmaceutical composition in a desired dosage form can be prepared.

For example, in the case of a composition for injection, optional components that are generally used in injectable preparations, such as an isotonic agent such as sodium chloride; a buffering agent such as a phosphoric acid salt or a citric acid salt; a pH adjusting agent; a saccharide such as glucose; a stabilizer; and a solubilizer, can be used. For administration as an injectable preparation, the pharmaceutical composition of the present invention may be prepared as a liquid obtained by dissolving the composition in an aqueous carrier such as physiological saline and sterilizing the solution, or may be prepared as a powder preparation for injection, which is dissolved in an aqueous carrier at the time of use.

Furthermore, for example, oral preparations such as a powder preparation, a granular preparation, a tablet preparation and a capsule preparation can be formulated according to standard methods, using saccharides such as starch, carboxymethyl cellulose and corn starch; inorganic salts, and the like. In these preparations, in addition to the excipients such as those described above, a binder, a disintegrant, a surfactant, a lubricating agent, a fluidity promoting agent, a coloring material, a flavor, and the like can be appropriately used.

The methods for preparing these various preparations are sufficiently known to those ordinarily skilled in the art. Meanwhile, when the term "pharmaceutical composition" is used in relation to the present invention, the term is meant to include those compositions for application to human being, as well as for application to an animal other than human being.

The pharmaceutical composition of the present invention is preferably administered such that a predetermined concentration in blood is maintained. A preferred concentration in blood may be about 20 ng/ml to about 200 ng/ml, and preferably about 50 ng/ml to about 100 ng/ml.

The dosage amount of the pharmaceutical composition of the present invention may vary depending on the form of preparation, route of administration, and the kind, age, body weight, disease condition and the like of the subject of administration, and the pharmaceutical composition can be administered in respectively appropriate amounts depending on those conditions. In order to maintain the concentration in blood such as described above, the dosage amount can be set to, for example, 2 mg or more per kilogram of body weight per day. When the pharmaceutical composition is administered to a human being, generally, the amount may be 80 mg to 160 mg per day as the amount of the active ingredient, and for example, the amount may be 120 mg or more per day for an adult. Such a daily dose can be administered in a signal or divided doses, to a subject who is in need of prevention or treatment.

The mechanism by which STC1 ameliorates fibrosis is speculated as follows. STC1 decreases the mitochondria membrane potential by up-regulating UCP2, and thereby reduces the amount of peroxides (ROS). Also, STC1 exhibits a disturbance alleviating action by inducing uncoupled respiration and improving the energy efficiency in a disturbed environment. As a result, fibrillization of cells is ameliorated. Such a mechanism is completely different from the operating mechanism of the known activities of STC1.

EXAMPLES

1. Fibrillization Suppressing Effect of STC1 in Disease Model Mouse

The action of STC1 was investigated using a pulmonary fibrosis model utilizing the mitotic inhibitory action of an anticancer agent, bleomycin (Bleo), as the disease model mouse.

Human recombinant (r) STC1 was produced by BioVender, Inc. Specifically, human-derived STC1 gene added with a TAG structure was introduced into the 293 cells, and rSTC1 was separated using the TAG sequence.

Specifically, C57BL6/J mice (female, 10 weeks old), four animals in each group, were anesthetized by intraperitoneally administering an anesthetic agent (obtained by diluting 300 µg of ketamine hydrochloride and 160 ng of xylazine in 100 µL of physiological saline). Thereafter, the cervix was cut open to expose a trachea, and the jacket of a 23G SURFLO needle was inserted into the trachea. Then, the following drugs were respectively administered intratracheally through the SURFLO jackets to the mice of each group.

(1) Saline control group: 50 µL of bleomycin-containing physiological saline (bleomycin concentration: 400 ng/mL)

(2) STC1-administered group: 500 ng of STC1+50 µL of bleomycin-containing physiological saline (3) NAC-administered group (positive control): 3 mg of NAC+50 µL of bleomycin-containing physiological saline (4) Normal lung group: 50 µL of physiological saline After one week, the mice were euthanized by anesthetizing the mice as described above and then cutting the carotid artery, and subsequently, the lungs were removed. The extirpated lung tissues were subjected to histopathologic staining (HE (hematoxylin eosin) staining, EM (Elastica-Masson staining), and 8OHDG staining) by standard methods. The stained lung tissues were observed with an optical microscope.

The results are presented in FIGS. 1 to 6 and FIG. 7.

HE staining shows the overall image of the tissue. EM staining shows the extent of fibrillization, so that a darker color implies that the amount of elastic fibers has increased, and fibrillization of the lung has been exacerbated. Furthermore, 8OHDG staining shows the amount of peroxides, and as there are more peroxides, the tissue is stained more darkly.

In FIGS. 1 to 6, panel A presents HE staining, and panel B presents EM staining. In the saline control group (FIGS. 3 and 4), fibrillization was induced, whereas in the STC1-administered group (FIGS. 1 and 2) and NAC-administered group (FIG. 5), fibrillization was suppressed. That is, intratracheal administration of STC1 suppressed the progression of pulmonary fibrosis in the bleomycin pulmonary fibrosis model, and STC1 showed complete response, while NAC showed amelioration.

Figure 1:
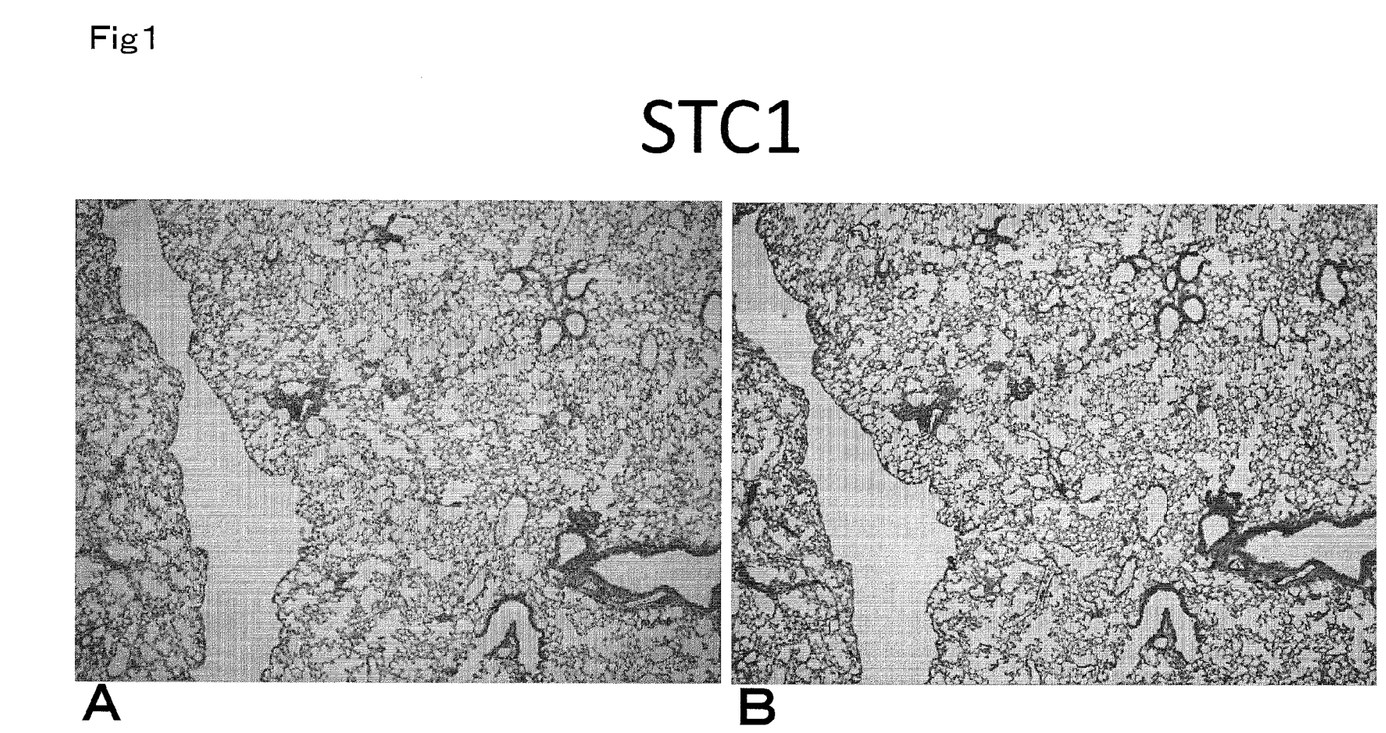
FIG. 1 is a diagram showing stained images of the pulmonary tissue of an animal subject of the STC1-administered group. Panel A represents a hematoxylin eosin (HE) stained image, and panel B represents an Elastica-Masson (EM) stained image (the same applies to FIGS. 2 to 5)
Figure 2:
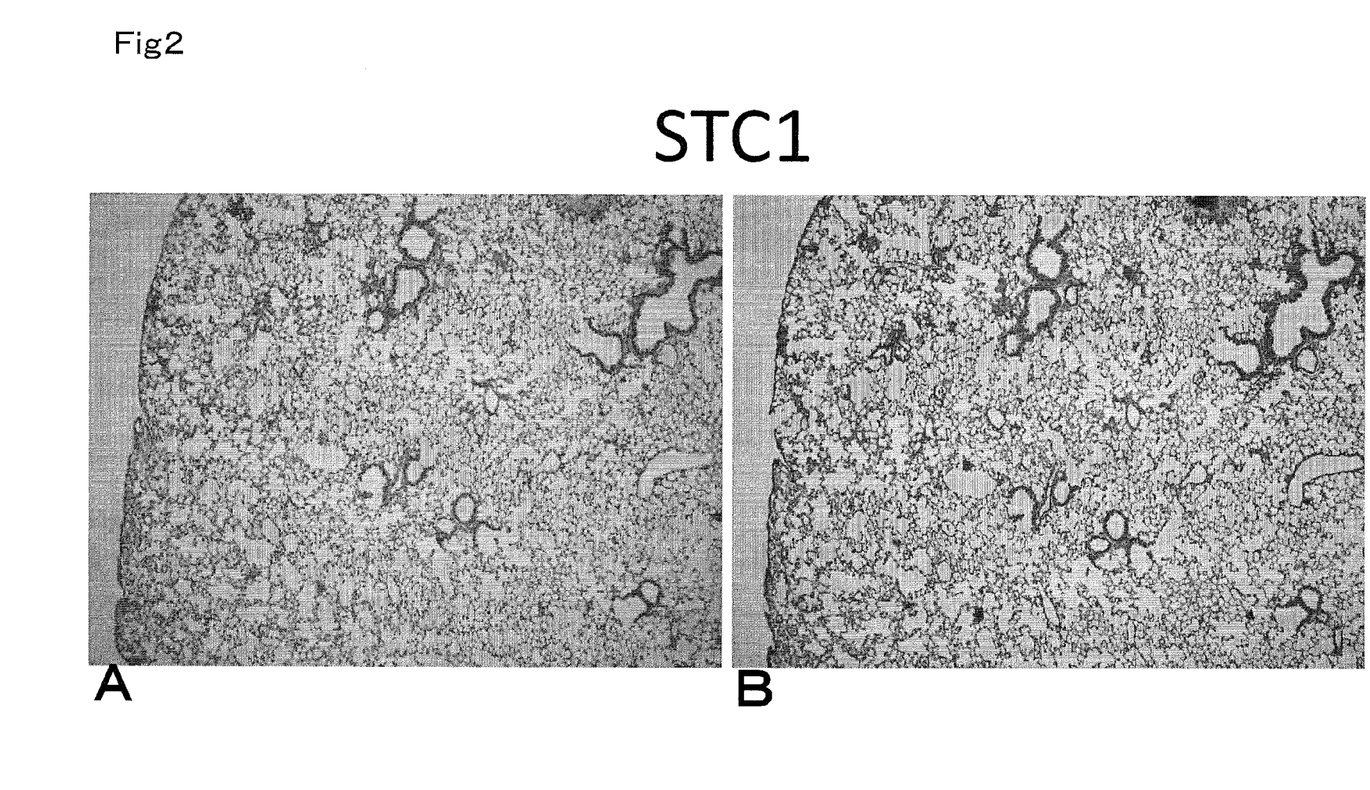
FIG. 2 is a diagram showing stained images of the pulmonary tissue of another subject of the STC1-administered group.
Figure 3:
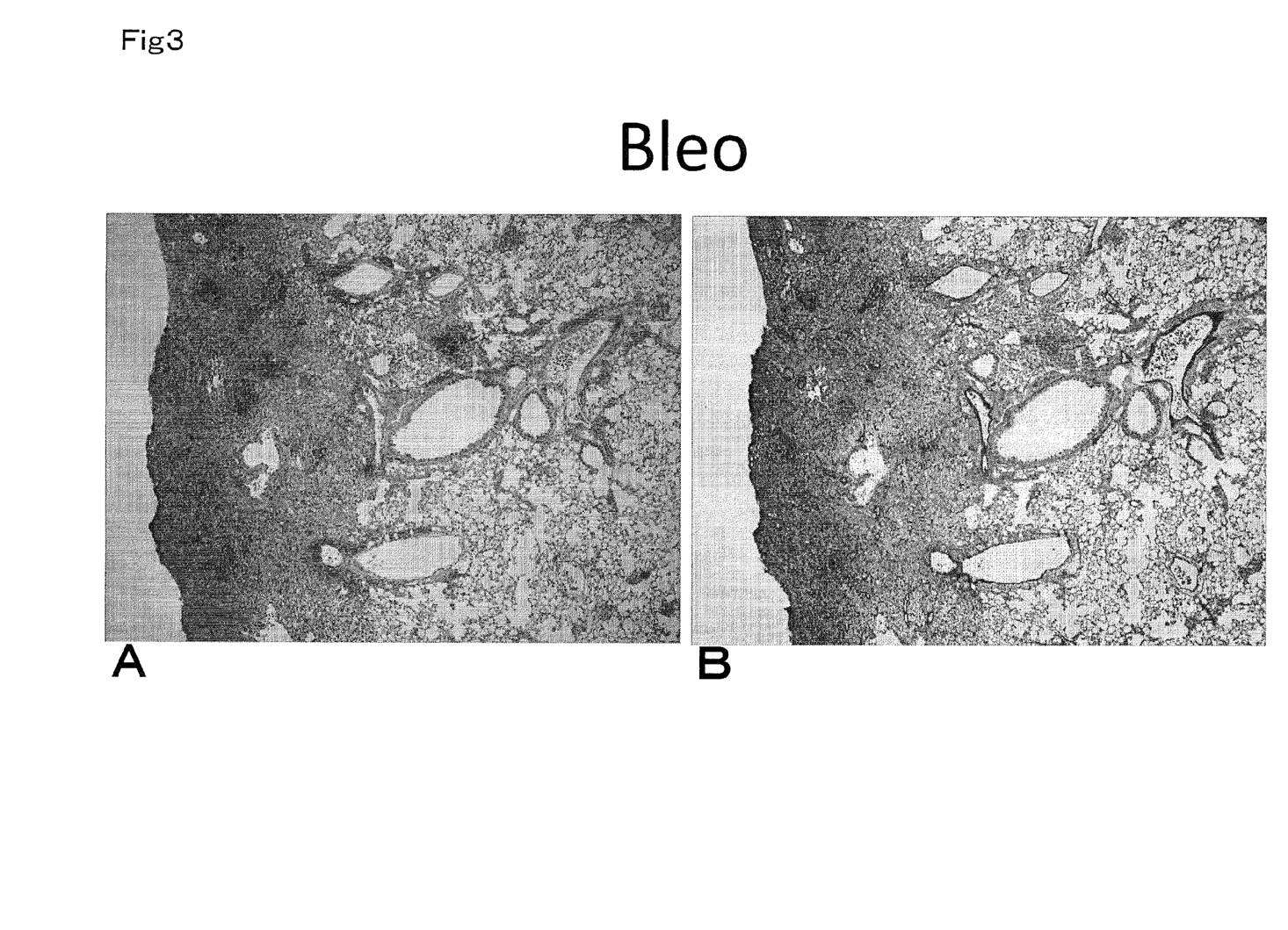
FIG. 3 is a diagram showing stained images of the pulmonary tissue of an animal subject of the bleomycin (Bleo)-administered group.
Figure 4:
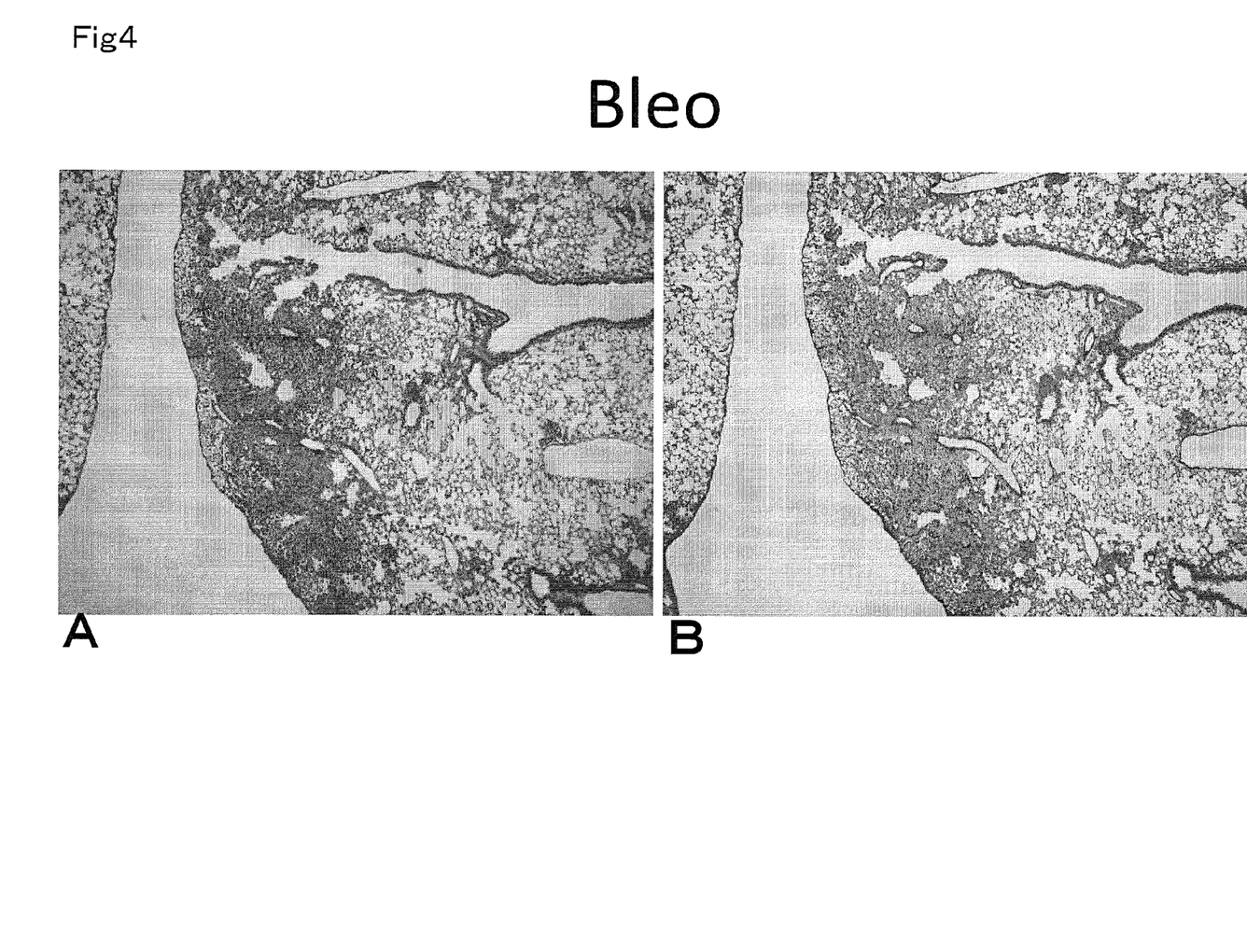
FIG. 4 is a diagram showing stained images of the pulmonary tissue of another subject of the bleomycin (Bleo)-administered group.
Figure 5:
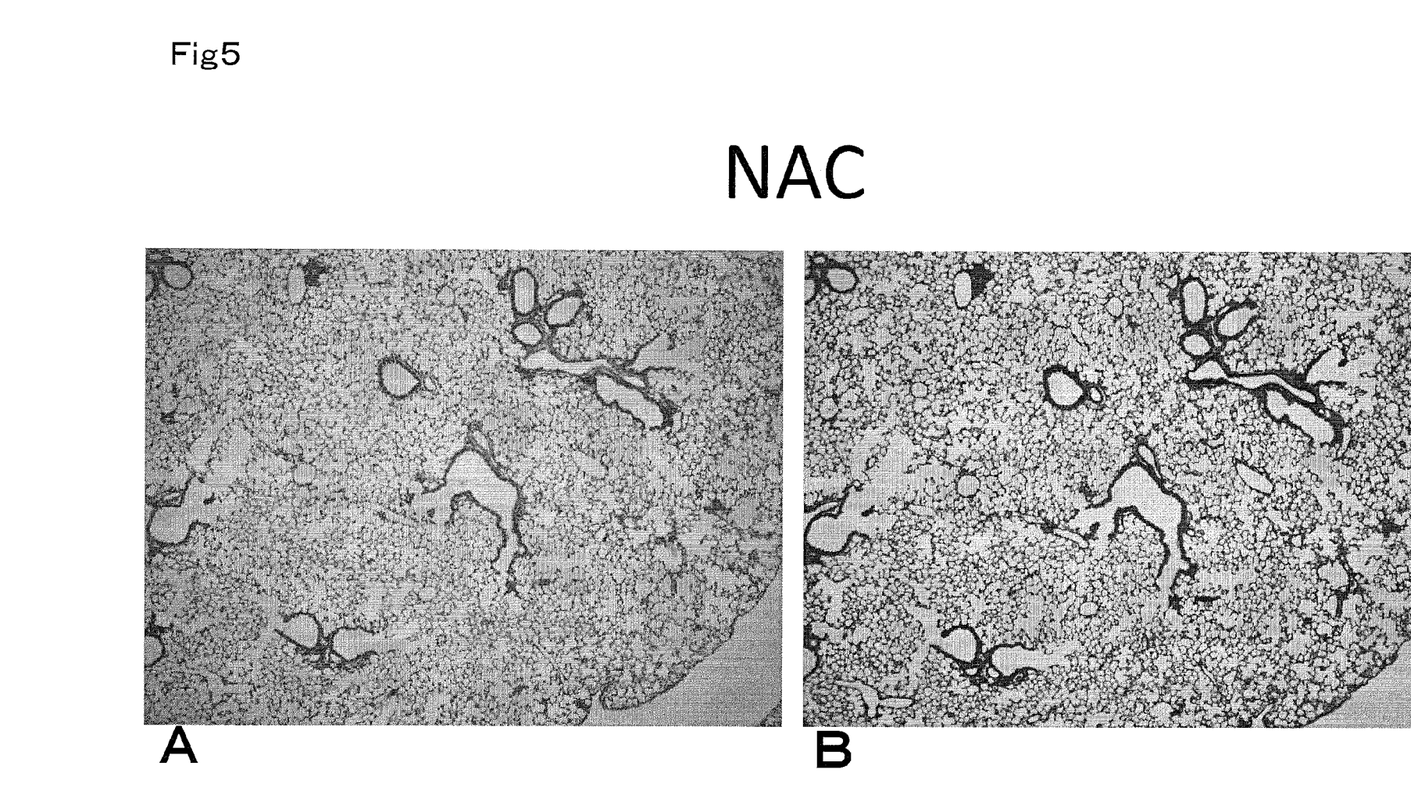
FIG. 5 is a diagram showing stained images of the pulmonary tissue of an animal subject of the N-acetylcysteine (NAC)-administered group.
Figure 6:
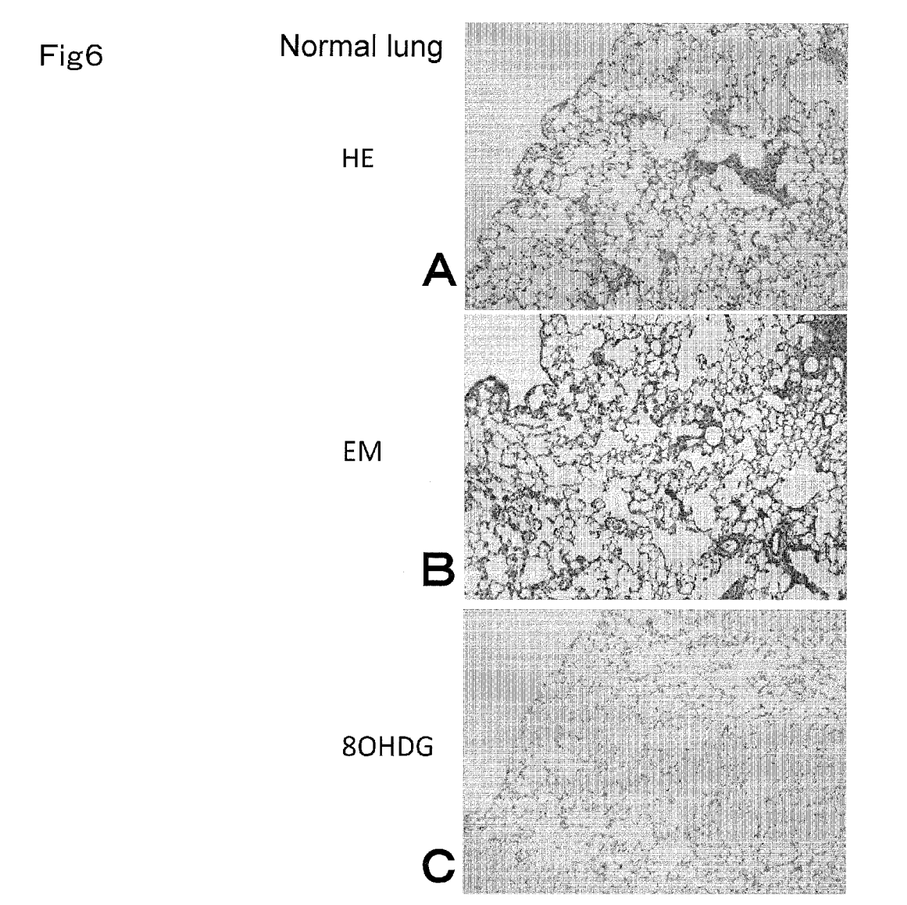
FIG. 6 is a diagram showing stained images of normal pulmonary tissue. Panel A represents a HE stained image, panel B represents an EM stained image, and panel C represents an 8-hydroxydeoxyguanosine (8OHDG) stained image.
Figure 7:
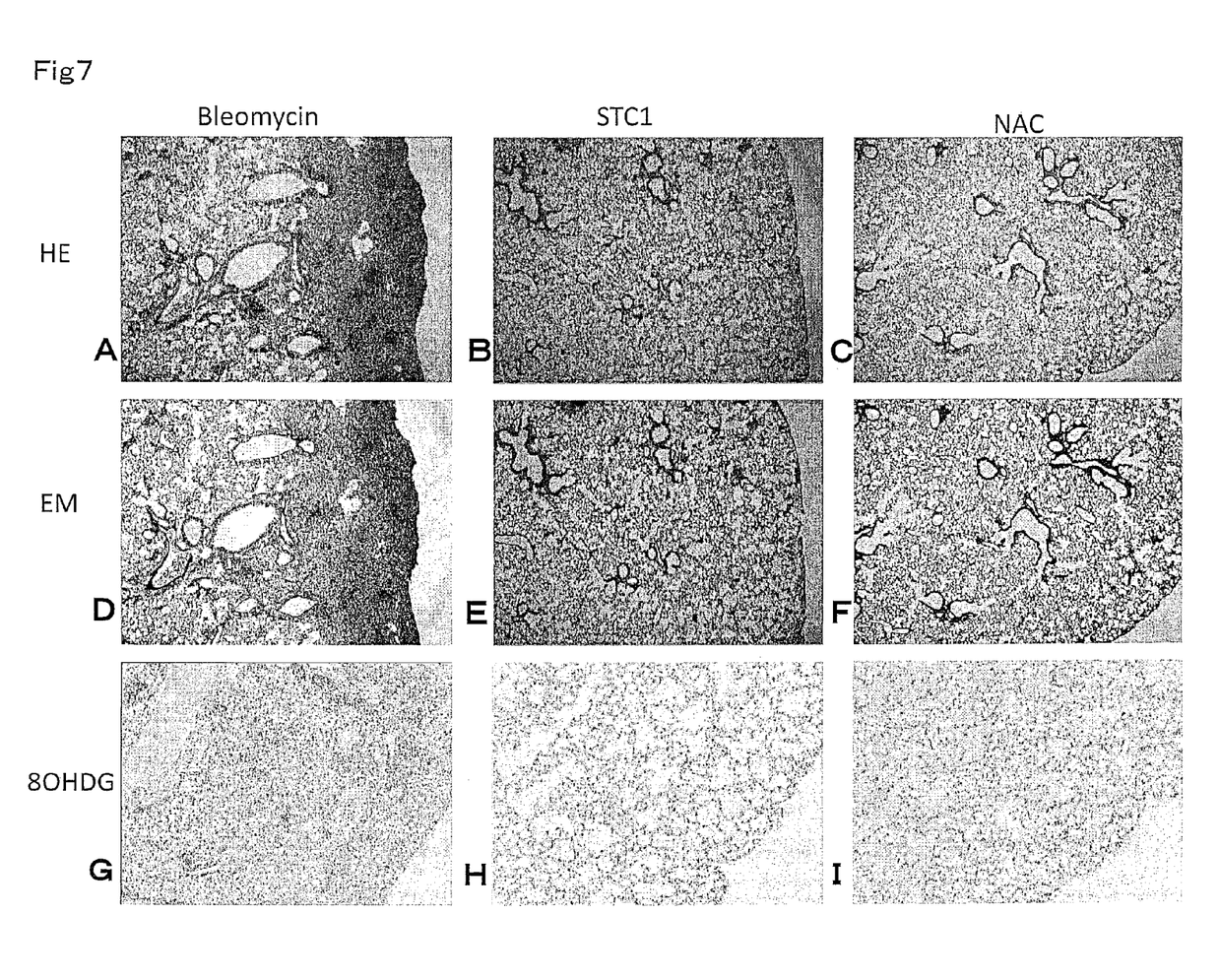
FIG. 7 is a diagram showing stained images of the pulmonary tissues of the bleomycin-administered group (panels A, D and G), the STC1-administered group (panels B, E and H) and the NAC-administered group (panels C, F and I). Panels A to C represent HE stained images, panels D to F represent EM stained images, and panels G to I represent 8OHDG stained images.

In FIG. 7, the results of 8OHDG staining are shown together. When the lung tissues were stained with 8OHDG, the saline control group (panel G) was stained significantly, but the STC1-administered group (panel H) and the NAC-administered group (panel I) were poorly stained, to an extent similar to that of the normal lung group (FIG. 6, panel C). Therefore, it was suggested that STC1 is capable of suppressing peroxidation stress by bleomycin, as in the case of NAC.

The above-described results are summarized in Table 2.

TABLE 2

| Staining | Group | | | |
|---|---|---|---|---|
| | Saline control group (Bleo) | STC1-administered group (STC1) | NAC-administered group (NAC) | Normal lung group |
| HE (fibrillization) | +++ | + | +~++ | − |
| EM (fibrillization) | +++ | + | +~++ | − |
| 8OHDG (extent of peroxides accumulation) | +++ | + | + | − |

−: not observed
+: mild
++: moderate
+++: severe

This patent application is based on Japanese Patent Application No. 2011-152392 filed Jul. 9, 2011, and the entire disclosure of the specification and claims of Japanese Patent Application No. 2011-152392 is incorporated herein.

The invention claimed is:

1. A method for treating and/or suppression of progression of pulmonary fibrosis, comprising: administering to a subject in need thereof a composition comprising stanniocalcin 1 (STC1).

\* \* \* \* \*